(12) United States Patent
Spahn

(10) Patent No.: US 8,277,220 B2
(45) Date of Patent: Oct. 2, 2012

(54) IMPLANT, IN PARTICULAR JAW IMPLANT, WITH DIFFERENT MATERIAL PROPERTIES

(76) Inventor: Frank-Peter Spahn, Hasselt (BE)

( * ) Notice: Subject to any disclaimer, the term of this patent is extended or adjusted under 35 U.S.C. 154(b) by 307 days.

(21) Appl. No.: 12/226,505

(22) PCT Filed: Apr. 19, 2007

(86) PCT No.: PCT/EP2007/053848
§ 371 (c)(1),
(2), (4) Date: Nov. 4, 2008

(87) PCT Pub. No.: WO2007/122178
PCT Pub. Date: Nov. 1, 2007

(65) Prior Publication Data
US 2009/0170054 A1    Jul. 2, 2009

(30) Foreign Application Priority Data
Apr. 21, 2006   (DE) .................. 10 2006 018 516

(51) Int. Cl.
*A61C 8/00* (2006.01)
(52) U.S. Cl. .................. 433/176; 433/201.1; 623/17.17
(58) Field of Classification Search .......... 433/172–176, 433/201.1; 623/16.11, 17.17, 23.58, 23.59
See application file for complete search history.

(56) References Cited

U.S. PATENT DOCUMENTS

| | | |
|---|---|---|
| 408,990 A | 8/1889 | Rundquist |
| 4,323,080 A | 4/1982 | Melhart |
| 4,408,990 A | 10/1983 | Misch |
| 4,702,697 A | 10/1987 | Linkow |
| 4,722,687 A | 2/1988 | Scortecci |
| 4,789,337 A | 12/1988 | Scortecci |
| 4,815,974 A | 3/1989 | Scortecci |
| 5,006,984 A | 4/1991 | Steele |
| 5,591,233 A | 1/1997 | Kelman et al. |
| 6,193,516 B1 | 2/2001 | Story |
| 6,402,516 B2 | 6/2002 | Ihde |

(Continued)

FOREIGN PATENT DOCUMENTS

CH    690 416    9/2000

(Continued)

OTHER PUBLICATIONS

International Search Report.

(Continued)

*Primary Examiner* — Cris L Rodriguez
*Assistant Examiner* — Hao D Mai
(74) *Attorney, Agent, or Firm* — Collard & Roe, P.C.

(57) ABSTRACT

The invention relates to an implant (1), particularly a jaw implant, which comprises several structural zones (5, 6, 12) made of a material which is non-resorbable, particularly from bones, for the implantation on bones or at least in the vicinity of bones. In an advantageous further embodiment of the implant, two or more of said structural zones (5, 6, 12) have respectively different material properties, in particular different physical properties such as different deformation and/or strength properties. The invention also relates to a method for determining load-dependent deformations in different bone regions, according to which X-ray images of the bone regions are taken with and without mechanical load for comparison. By comparing the X-ray images taken of the individual bone regions under or without load, the resulting deformation can be determined due to the applied load.

10 Claims, 8 Drawing Sheets

U.S. PATENT DOCUMENTS

| | | |
|---|---|---|
| 6,641,893 B1 | 11/2003 | Suresh et al. |
| 6,839,457 B1 | 1/2005 | Azuma et al. |
| 7,621,950 B1 * | 11/2009 | Globerman et al. ....... 623/17.11 |
| 2001/0038996 A1 | 11/2001 | Ihde |
| 2005/0106535 A1 | 5/2005 | Ihde |
| 2006/0074311 A1 | 4/2006 | Sakai et al. |
| 2007/0055254 A1 | 3/2007 | Ihde |
| 2007/0264613 A1 | 11/2007 | Ihde |
| 2010/0145393 A1 | 6/2010 | Fallin |

FOREIGN PATENT DOCUMENTS

| | | |
|---|---|---|
| DE | 35 27 668 | 2/1987 |
| DE | 298 20 487 | 3/1999 |
| DE | 199 48 910 | 12/2000 |
| DE | 203 04 367 | 7/2004 |
| DE | 103 34 366 | 2/2005 |
| DE | 20 2006 003 922 | 7/2007 |
| EP | 0 083 028 | 7/1983 |
| EP | 0214962 | 3/1987 |
| EP | 0 083 028 B1 | 8/1987 |
| EP | 0 570 172 | 11/1993 |
| FR | 2302715 | 1/1976 |
| FR | 2 600 523 | 12/1987 |
| WO | WO 2007/060507 | 5/2007 |

OTHER PUBLICATIONS

Article in German "Zahnarztiche Praxis" by Dr. Frank-Peter Spahn, 1996.

* cited by examiner

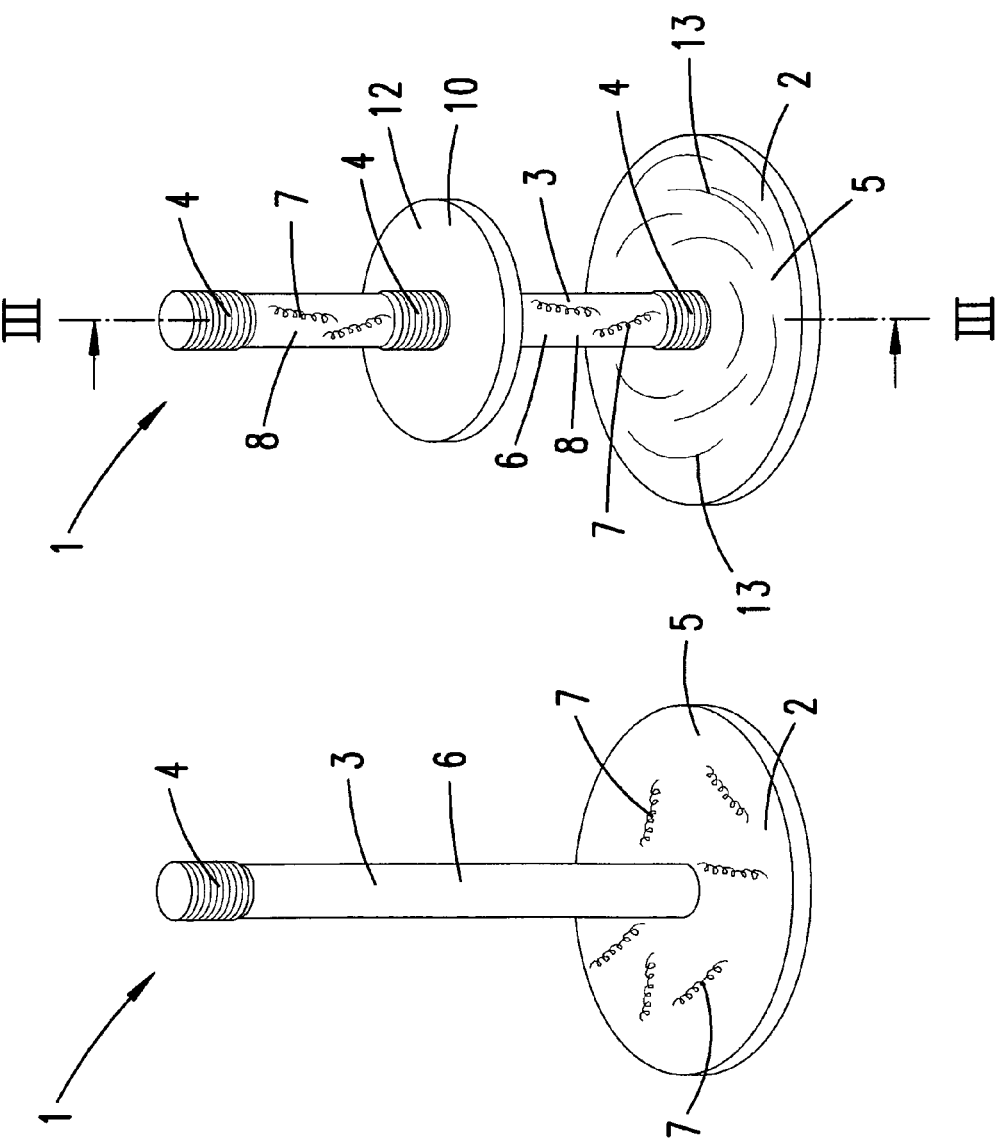

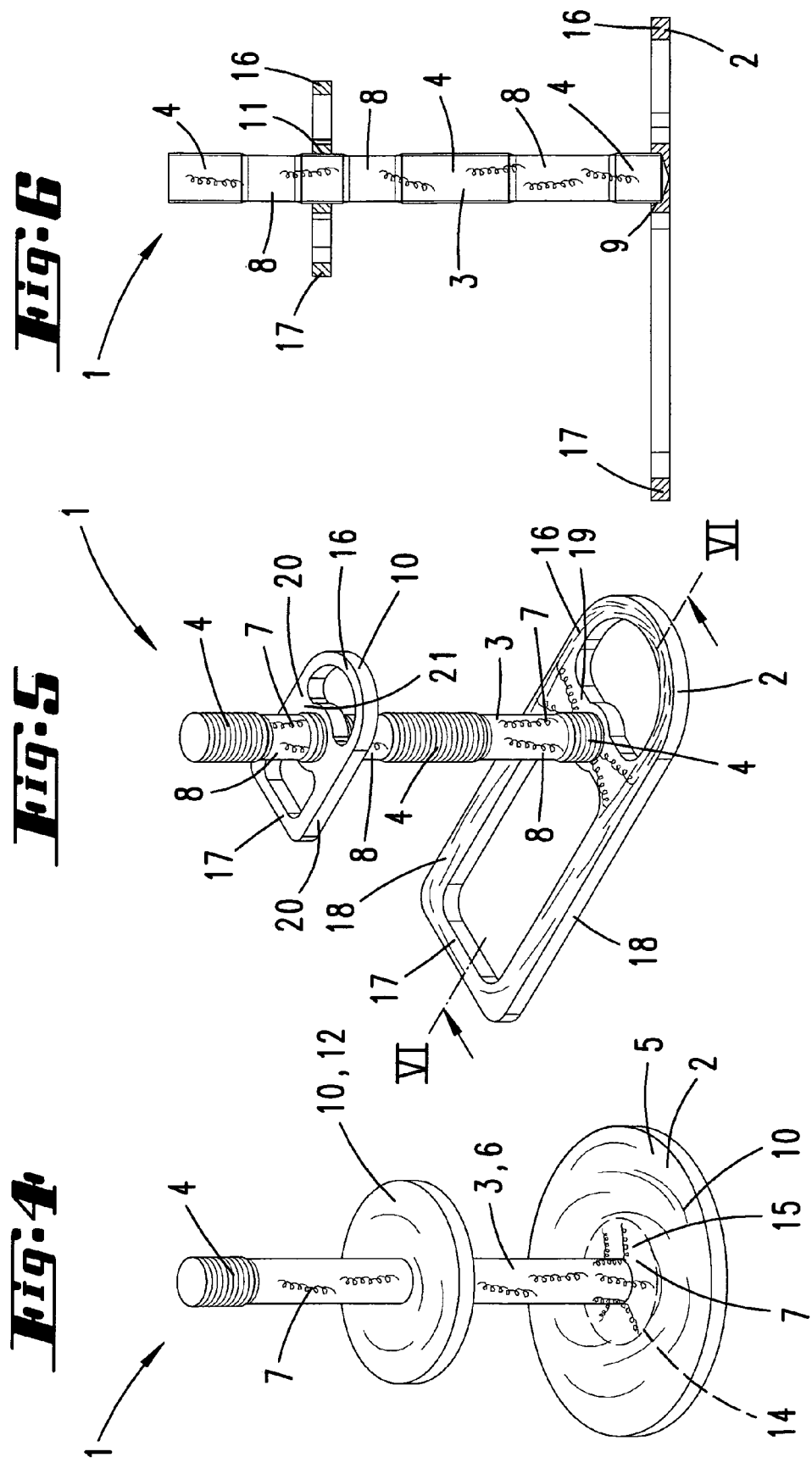

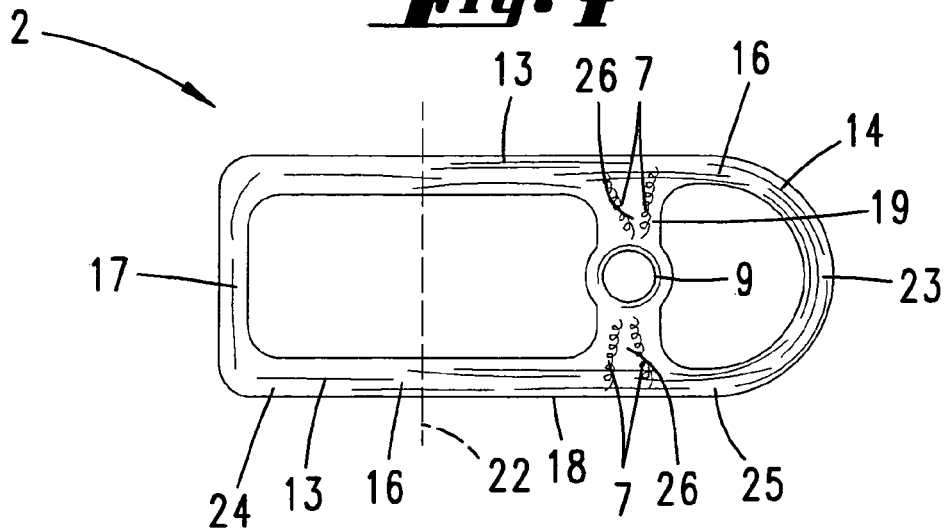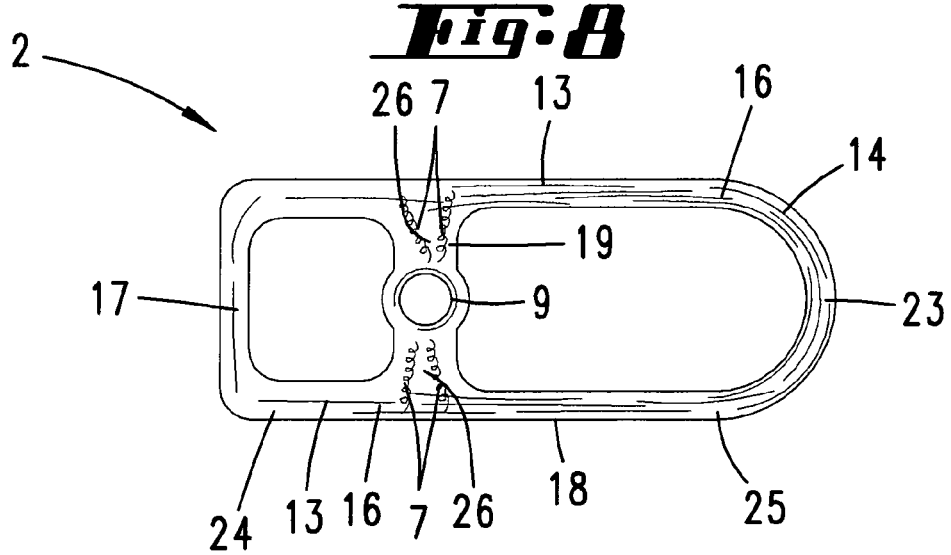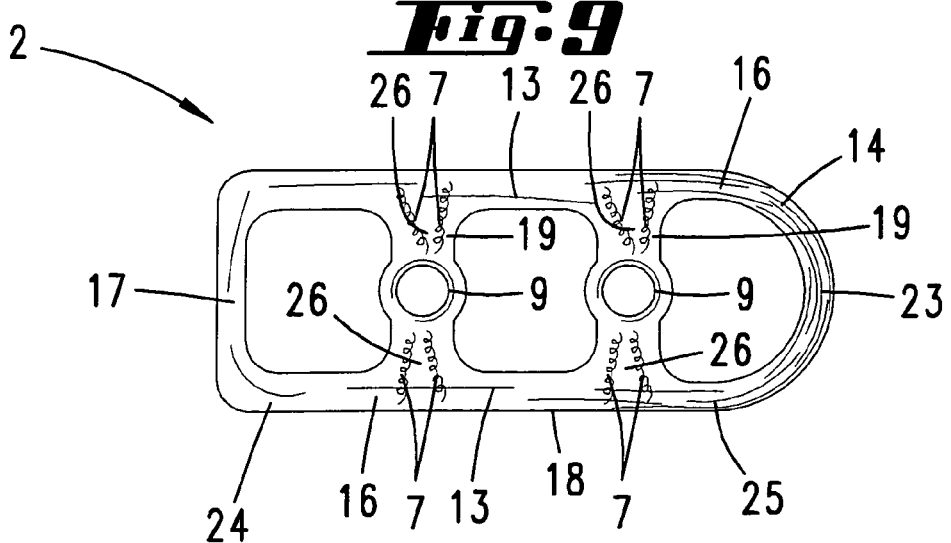

IMPLANT, IN PARTICULAR JAW IMPLANT, WITH DIFFERENT MATERIAL PROPERTIES

CROSS REFERENCE TO RELATED APPLICATIONS

This application is the National Stage of PCT/EP2007/053848 filed on Apr. 19, 2007, which claims priority under 35 U.S.C. §119 of German Application No. 10 2006 018 516.1 filed on Apr. 21, 2006. The international application under PCT article 21(2) was not published in English.

The invention relates to an implant, in particular a jaw implant, which has a number of structural regions which are made of a material that cannot be resorbed by bones, or not to any substantial extent, and are suitable for implantation in or alongside bones.

In the prior art, such implants for jaw implantation, i.e. jaw implants, are known in a one-part configuration from CH 690416 A5 and in a multi-part configuration from DE 19948910 A1. The implants described there have a plate-like foot part, used for basal anchoring, a shaft which extends perpendicularly from the plane of the foot part, at the free end of which, remote from the foot plate, a so-called abutment or threaded portion is provided for securing an artificial tooth or a prosthetic dental construction, and optionally in addition one or more likewise plate-like intermediate parts, which are held on the shaft between the foot plate and the free end. The implants may be fitted in the jaw in appropriately shaped, for example milled, cavities and remain there as an anchorage that is as durable and stable as possible. To enhance stability, the geometrical dimensions may be selected such that the implant extends through extensive parts of the jaw cross-section. In its structural regions that have a long-term load-bearing function, i.e. are not resorbed by the bone, these implants are produced from a material that is the same throughout, especially from titanium, which has a suitable certification. Even if the known implants already offer a series of advantages in terms of handling and use, under certain preconditions it is possible for early or late loss of the entire implant to occur after a certain period of use by the patient, caused by the dynamic loading of the jaw and implant during opening and closing of the mouth and chewing action.

On this basis, it is an object of the invention to develop implants of the type mentioned at the beginning in such a way as to avoid the stated disadvantages as far as possible.

The object is achieved according to the invention first and foremost by two or more of the structural regions, which are made of a material that cannot be resorbed by bones, or not to any substantial extent, and are suitable for implantation in or alongside bones, having material properties that are different from one another, preferably physical properties that are different from one another, such as different deformation and/or strength properties. The structural regions of a one-part or multi-part implant that are referred to here are firstly those regions that are intended or positionally adapted for being fitted in bone cavities and/or secured alongside or adjacent bones during the implantation. This does not preclude the possibility of implants according to the invention from also having further structural regions, for example protruding from the jaw, and of such structural regions also being included in the variation of material properties. There is also the possibility of structural regions, for example on artificial teeth, prosthetic dental constructions, etc., that are carried by the jaw implant (i.e. are not themselves a component part of the jaw implant) also being additionally included in the gradation of material properties. The structural regions referred to at the beginning may be implant regions that differ locationally, i.e. are spaced apart from one another and/or adjacent one another. The invention is based on the fact that natural bones constitute an inhomogeneous material with respect to the physical properties, in particular the deformation and strength properties, i.e. different material properties may be present in different regions of the bone, in particular alongside or adjacent an implantation site that is provided in the bone. With the proposed solution, the invention creates the possibility of adapting the material properties of an implant, at least in certain individual structural regions, to the local differences in the surrounding bone, i.e. of providing an implant that is to this extent osteomimetic. The concept of physical properties is to be understood here in a broad sense, insofar as bone material can also be characterized in its behavior, in particular with and without mechanical loading, by various different material properties. Although in the area of jaw implants the possibility of this adaptation also exists in principle in the case of so-called crestal implants, it is preferably intended for use in the case of so-called basal jaw implants, i.e. those with a foot part serving for anchoring. In addition to jaw implants, use of the invention is also possible in principle in the case of implants intended for other regions of the body.

There is preferably the possibility of the implant having, in the at least two or more different structural regions referred to, different elasticity from one another, preferably a different level of modulus of elasticity, and/or different viscoelastic behavior and/or different toughness and/or different stiffness and/or different strength, preferably different flexural and/or torsional strength, and/or different hardness and/or different brittleness. Against the background that the elastic behavior is not the same in different regions of the jaw, it is possible according to the invention for example for an implant with an elastic behavior adapted in different structural regions to the elastic behavior of associated bone regions on the implant bed to be produced, i.e. an implant which to this extent displays "isoelastic behavior" with the surrounding jaw bone. A different elasticity may, for example, include a different level of the modulus of elasticity, a force-deformation relationship that is markedly linear to a different degree, in particular a certain degree of viscoelastic behavior, and in particular an ability to recover by itself after deformations, i.e. resilience, that is markedly strongly different. A structural material which contains ketone, in particular polyetherether ketone, or a mixture of polyetherether ketones, or a plastics material such as Delrin is preferred as the material or base material for producing the implant, at least in the said structural regions. For example, a polyaromatic, semicrystalline thermoplastic based on polyetherether ketones that is offered by the company Invibio Ltd under the name PEEK-OPTIMA® comes into consideration. The implant is preferably entirely or partially produced from a material which consists of polyetherether ketones (PEEK) or contains the latter as the base material in a preferably predominant proportion in terms of the amount. Apart from the biocompatibility that is advantageous for the said use, this material can be adapted to the material properties of the bone, in particular its modulus of elasticity, by means of suitable additives. It is consequently possible in the case of the implant according to the invention to avoid the overload reactions that can be explained in the case of conventional implants, for example consisting of a metal material that is the same throughout, by the different behavior of the bone and the implant under loading. Within the scope of the invention, different material properties can be established in different structural regions of the implant just by corresponding variations in the composition of the polyetherether ketone or by a different chain length or different mixtures with different chain lengths. Apart from polyetherether ketones (PEEK for short), in principle polyether ketones and polyether ketone ketones, the respective structural formula of which can be taken from the technical literature (for example Römpp: Chemielexikon), can also be taken into consideration. For the processing of such materials, the injection-molding process for example, or other processes familiar to the person skilled in the art, come into consideration. To achieve different material properties at different structural regions of the implant, in each case a different polyetherether ketone, or in each case different mixtures of polyetherether ketones, for example of different chain lengths, may be used. Alternatively or in combination, to achieve different material properties in different structural regions of the implant, an additive may be added to the plastics material in those regions, in particular the polyetherether ketone or the mixture of polyetherether ketones, the additive being distributed in the plastics material. Fibrous filaments in the form of carbon fibers and/or glass fibers and/or for example titanium fibers, or other substances, organic or inorganic additives with or without a fibrous structure are preferred as the additive. If, for example, the material PEEK-OPTIMA® is used, a material appropriate for the respective requirements could be produced for different regions of the jaw with differing elastic behavior by corresponding variations in the composition or additives. The advantage of PEEK for the use according to the invention is also that, on account of its biocompatible properties, it is suitable together with inclusions of various types for the production of composite materials with different material properties. Apart from the carbon or glass fibers already referred to as inclusions, titanium in filament form also comes into consideration. With such inclusions, it is possible for example to influence, in particular increase, the strength and the toughness of the composite material, and consequently adapt the physical properties in different structural regions of the implant to the specific conditions in the bone. With regard to the fibrous filaments, there is the possibility of using them in the form of plain fibers and/or spirally formed fibers and/or helically coiled fibers. While the stability in particular can be increased by plain filaments, i.e. filaments that are at least substantially straight, it is possible by adding spiral or coiled filaments to improve the elastic behavior, in particular the resistance to torsion. Spiral or coiled filaments can preferably be used in structural regions of an implant in which shear forces occur in the surrounding bone in addition to compressive and tensile forces, specifically including during chewing action. Materials that are not homogeneous, such as bone for example, react to such force effects by twisting. If coiled or spiral filaments are incorporated in the structural regions, these structural regions can withstand twisting for longer without rupturing than if plain filaments are added. To this extent, the coiled or spiral filaments improve the elastic behavior or the elasticity of the material. According to the statements made above, to achieve different material properties in different structural regions of the implant, it is preferable that different polyetherether ketone or different mixtures of polyetherether ketones are provided and/or the type and/or amount of additives is differently selected in these regions.

In a preferred embodiment of the invention, the implant is a one-part or multi-part jaw implant, preferably a basally anchored jaw implant. However, use for so-called crestal implants, without a basal plate-like foot part, would also be conceivable. With regard to a jaw implant that can be basally anchored, it is preferred that it has at least one basal, preferably plate-like, foot part and a shaft extending from the foot plate, and, merely preferably, also one or more intermediate parts, which are held on the shaft as a distance from the foot part and preferably spaced apart from one another, the intermediate parts likewise being preferably plate-like. In this connection, configurations of foot or intermediate parts which substantially comprise a peripheral frame and webs protruding into a central opening are considered to be plate-like. The foot part, and optionally the intermediate part or parts, have a substantially planar extent, which preferably runs perpendicularly to that of the shaft. It is also preferred that the intermediate part or parts project outward from the shaft less far than the foot part. In connection with the aforementioned features, it is preferred that the two or more structural regions according to the invention that have different material properties from one another are located on these component parts of the implant. Especially multi-part implants that can be basally anchored (so-called basal modular implants) are particularly suitable for giving the implant different physical properties in its structural portions (although one-part and crestal implants are also suitable in principle). As far as multi-part jaw implants are concerned, the invention can preferably also be applied to implants of the type known from DE 19948910 A1 for lateral insertion into milled jaw cavities. The disclosure of this document is to this extent incorporated in the present application, including for the purpose of incorporating features in claims. In this connection, it is preferred that the shaft is provided with an external thread, preferably the shaft has one or more externally threaded zonal portions and one or more adjacently spaced-apart smooth annular zones, and that the foot part and/or the intermediate part or parts have an internal thread matching the external thread, preferably have internally threaded zonal portions that can be associated with the shaft in the region of its threaded zonal portions at a variable spacing from one another. Among many further possibilities for use, the present invention can, in the sense of a simple exemplary embodiment, also be used for a one-piece implant such as that already known from CH 690416 A5, the disclosure of which is in this sense incorporated in the present application. Independently of a one-part or multi-part configuration of the implant, there is the possibility that the shaft and/or the foot part and/or one or more intermediate parts have at least in certain regions different material properties from one another, preferably different properties from among those mentioned above. For example, the foot part may have a greater strength than the shaft and, conversely, the latter may have a more pronounced elastic behavior. Alternatively or in combination, there is the possibility that the shaft and/or the foot part and/or the intermediate part or parts have in them, i.e. within their respective structural portion, structural regions with different material properties from one another, preferably different material properties from one another from among those mentioned above. For example, the foot part may have a higher strength in one of its peripheral regions than in its opposite peripheral region for example. In an embodiment in which the shaft is connected to a web extending from the frame of the foot part, it is for example suitable if the web has comparatively more elastic material properties in comparison with the rest of the foot part, in order to improve the recoverability after lateral deflections of the shaft (for example caused by chewing movement). An embodiment in which the jaw implant is stiffer on one side, which is geometrically adapted for implantation on the lingual side of the jaw, in particular produced from stiffer material, than on the opposite side, which is in particular also geometrically adapted by comparison for implantation on the buccal side of the jaw, is also considered to be suitable. In this connection, it is also preferred that the perpendicular shaft or thread carrier has, in turn, lower brittleness and higher elasticity than the basal plate. This allows better adaptation by the implant material to the internal torsions, flexions and movements during opening and closing of the mouth and the act of chewing, and the implant consequently does not become detached so easily from the implant bed in the jaw. On the other hand, the body/bone cells that rub against the implant material as a result of the internal movements do not become damaged on the foreign material that is too inelastic. These injuries have in the past represented a main reason for early and late losses in the entire crestal and basal implant regions in the case of titanium implants. The material mimicking the material properties of the adjacent bone, in particular the elasticity of the bone, in different structural regions of the implant represents a suitable solution in order to avoid these problems. Alternatively or in combination, there is the possibility of plain and/or spiral and/or helically coiled filaments being incorporated in the basal plate-like foot part. Plain fiber filaments, for example in combination with polyetherether ketone, may serve the purpose of achieving a stable base plate with at the same time a modulus of elasticity as in the surrounding jaw bone. Spiral or coiled filaments are suitable in particular for improving the recovery after loading, and to this extent the elastic behavior. Coiled filaments, and in particular spiral filaments, are also better suited than plain filaments for improving the resistance to torsion in the base plate (foot plate). It is also possible that the basal part is made in one piece with a shaft extending perpendicularly from it, preferably with a thread carrier for securing an artificial tooth or a prosthetic superstructure, and that coiled or spiral filaments incorporated in the foot part extend into the shaft. Such filaments can allow deflection of the shaft during the act of chewing and ensure that it springs back into the starting position. This also constitutes an improvement of the elastic behavior and adaptation to the elasticity of the body or bone tissue.

The invention also relates to a method for determining the load-dependent deformations in different bone regions, which is useful in particular for the production of the previously described osteomimetic implants, preferably jaw implants, which however can also be used in other contexts. It is proposed according to the invention that, in the case of the method, X-ray images of bone regions are taken without and with mechanical loading for comparison, and that, by comparing the X-ray images for individual bone regions, taken with and without loading, the deformation that has respectively taken place there under the loading applied is determined. The X-ray mages preferably show in each case a number of bone regions of comparative interest simultaneously. To record deformations in different directions of deformation, there is the possibility of taking respectively comparative X-ray images, in particular in directions of imaging that also differ, with correspondingly different loading directions. Alternatively or in combination, X-ray images may also be respectively taken without and with loads of different intensities for one loading direction. The method proposed within the scope of the invention is suitable firstly for determining the locally different bone deformability, i.e. the locational distribution of the deformability or flexibility. It is preferred that the X-ray images are digitized (or digitally produced at the start) and evaluated comparatively to determine the locally different deformations with the aid of computer technology, preferably using image processing software. Prints of analogous images may, for example, be scanned in, for digitization. On the basis of the deformations determined, which generally differ locally, the physician, or for example a laboratory technician, can select the material best suited for producing an osteomimetic implant for the selected implantation site. In particular, there is the possibility of selecting different materials or material compositions for different structural regions of the implant. In this connection, it is preferred that, within the scope of the method proposed by the invention, the local value of a characteristic material variable for deformation and/or strength properties, preferably a characteristic material variable for characterizing the elastic bone behavior, more preferably the local value of the modulus of elasticity, and/or a characteristic material variable for the viscoelastic bone behavior is respectively determined on the basis of the deformations determined and the associated level of loading in the various bone regions. In this way, the practitioner can establish the elastic quality of the corresponding bone region in which implantation is to take place, for example in an upper jaw or lower jaw. For use in the production of jaw implants, it is preferred that panoramic X-ray images of jaw regions, preferably of the bone regions surrounding an existing or planned implant bed, are taken with and without loading from chewing. Appropriate measurements necessary for this can be performed, for example, in radiological practices. There is the possibility of the local values at least of one of the aforementioned characteristic material variables for deformation and/or strength properties, preferably for the modulus of elasticity, being determined for a number of peripheral regions of an implant bed in the bone and these values then being used for producing an implant, preferably of a basal jaw implant, that is osteomimetically adapted to the bone surroundings of the implant bed, by different structural regions of the implant that are associated with the evaluated peripheral regions of the implant bed being at least approximated or adapted to the associated peripheral regions of the bone with regard to the values of the characteristic variable. In this connection, the invention also relates to an implant which has been produced with the aid of the method described above.

According to a preferred embodiment, the implant according to the invention has as component parts at least one plate-like foot part and a shaft for a prosthetic part, an abutment, or the like, wherein the shaft is secured and/or can be secured, in particular can be screwed, to the foot part transversely to a plane of principal extent. According to yet another preferred embodiment, the implant has as component parts at least one shaft, in particular a pin-like shaft, for securing a prosthetic part, an abutment, or the like, also a first, preferably plate-like mount, at least one second, preferably plate-like mount and at least one separate, preferably pin-like connecting part, wherein the shaft is secured or can be secured to the first mount, preferably can be screwed therein, and wherein the connecting part is respectively secured or can be secured to the first mount and to the second mount, preferably can be respectively screwed therein, for the connection of the first and second mounts in an arrangement in which they are spaced apart from one another. In this connection, it is preferred that the first and/or the second mount respectively has a number of connections disposed in a distributed manner on it, which are suitable for connecting the shaft and/or a connecting element. It is also preferred that, in the mounted state, the shaft extends in its longitudinal direction transversely, preferably perpendicularly, to a plane of principal extent of the first mount and/or to a direction of principal extent of the second mount. Alternatively or in combination, in the mounted state, the connecting part may extend in its longitudinal direction transversely, preferably perpendicularly, to a plane of principal extent of the first mount and/or to a direction of principal extent of the second mount. In a suitable configuration, the first mount and/or the second mount may have a one-piece foot part. For suitable development, the first mount and/or the second mount may comprise a sleeve part, which has a pocket-like recess, the pocket cross-section of which is geometrically adapted to a cross-section of the foot part, to achieve an inserted manner of mounting on a foot part, and the sleeve part has one or more distributed connections, which are suitable for connecting the shaft and/or a connecting part. There is the possibility of the shaft and, if respectively present, one or more connecting parts, one or more foot parts and one or more sleeve parts consisting of a material which contains plastics, preferably polyetherether ketone. Considered with preference are materials containing polyetherether ketone, the modulus of elasticity of which lies at least more or less or approximately within a range of values typical for jaw bones, for example in the range from 6 to 12 Gpa (therefore significantly lower than the modulus of elasticity of titanium) and, when used, give the implant the desired physical properties comparable to the surrounding bone. For example, materials offered by the company Invibio Ltd under the names PEEK-OPTIMA® and PEEK-CLASSIX® are suitable. To this extent, materials with a modulus of elasticity of about 4 Gpa are also still well suited. It is especially preferred that the material from which the shaft and/or one or more connecting parts are produced has a lower modulus of elasticity, preferably lower by a factor of 2 to 3, than the material from which the foot part or parts and, if present, the sleeve part or parts are produced. In this connection, it is also preferred that the, to this extent different, values of the modulus of elasticity of the different materials used for the different implant components in each case lie within the range of values of the modulus of elasticity typical for bones, that is to say in particular in the range from about 4 to 12 Gpa. Preferably, the foot part or parts and, if present, the sleeve part or parts have a comparatively less elastic property than the shaft and, if present, the connecting part or parts. It is also seen as a suitable development that the material from which the foot part or parts and, if present, the sleeve part or parts are produced additionally contains glass fibers and/or carbon fibers and/or titanium fibers. For example, the materials offered by the company Invibio Ltd under the names PEEK-OPTIMA® CA130 and PEEK-OPTIMA CF® are suitable. In the case of the foot part and the sleeve parts, the modulus of elasticity may preferably lie in the range of about 11 GPa. Depending on the need or requirements, the use of materials with a modulus of elasticity that is either lower or higher in comparison with the aforementioned materials would also be conceivable.

According to a further aspect, the invention relates to a foot part for an implant, preferably for an implant which has one or more of the features described above, wherein the foot part has a plate-like base part and at least one connecting piece, preferably at least one threaded connecting piece, for connecting a shaft or an abutment, or for directly connecting a prosthetic part, wherein the connecting piece protrudes transversely to the plane of the plate of the base part beyond the plate-like base part and wherein there is at least one reinforcing web rising up above the plate-like base part, which web merges at a longitudinal end into the connecting piece and extends in the direction of a middle region of the foot part that is oriented in a longitudinal direction of the base part. In a development of this, it may be provided that there is a second reinforcing web rising up above the base part, which web merges at a longitudinal end into the threaded connecting piece, and that the first and second reinforcing webs extend in line with one another in the direction of the middle region of the foot part that is oriented in the longitudinal direction of the base part. The foot part can be inserted laterally into a groove milled in the jaw as a basal anchorage for the implant, preferably in such a way that it is supported by the front and rear ends on the comparatively stronger peripheral regions (corticalis) lying opposite in the cross-section of the jaw. The reinforcing webs can then serve for evening out the load transfer from the implant to these two supporting locations and reduce the flexure of the foot part in the inner, soft bone cross-section (spongiosa). In this connection, it is also preferred that, in the region of the reinforcing web or webs, inclusions of fiber material, preferably of spiral and/or helically coiled fiber material, are embedded in the surrounding material, which preferably comprises polyetherether ketone (PEEK), wherein the fiber material may preferably extend from the reinforcing webs into the base part and/or into the threaded connecting piece. In this way it is possible in particular for the elastic properties to be favorably influenced, in which respect reference is also made to the foregoing description. It proves to be advantageous if, with respect to its direction of longitudinal extent, the fiber material is predominantly aligned in the longitudinal direction of the reinforcing webs. To this extent, the reinforcing webs, which for their part extend in the longitudinal direction, i.e. in the direction of insertion, of the foot part, facilitate the introduction of the inclusions provided in the respectively desired direction of intent.

The invention is further described below with reference to the accompanying drawings, which show preferred exemplary embodiments of the implant and in which:

FIG. 1 shows in perspective a one-piece jaw implant according to the invention as provided by a first preferred embodiment;

FIG. 2 shows in perspective a further preferred embodiment of a jaw implant, but in a multi-part configuration;

FIG. 3 shows the jaw implant shown in FIG. 2 in a longitudinal section taken through its shaft;

FIG. 4 shows in perspective a further preferred embodiment of a one-piece jaw implant;

FIG. 5 shows in perspective a further preferred embodiment of a multi-part jaw implant;

FIG. 6 shows the jaw implant shown in FIG. 5 in a longitudinal section taken through the shaft;

FIG. 7 shows a plan view of the foot part of the implant represented in FIG. 5;

FIG. 8 shows a modification of the foot part represented in FIG. 7;

FIG. 9 shows a second modification of the foot part shown in FIG. 7;

Figure 10:
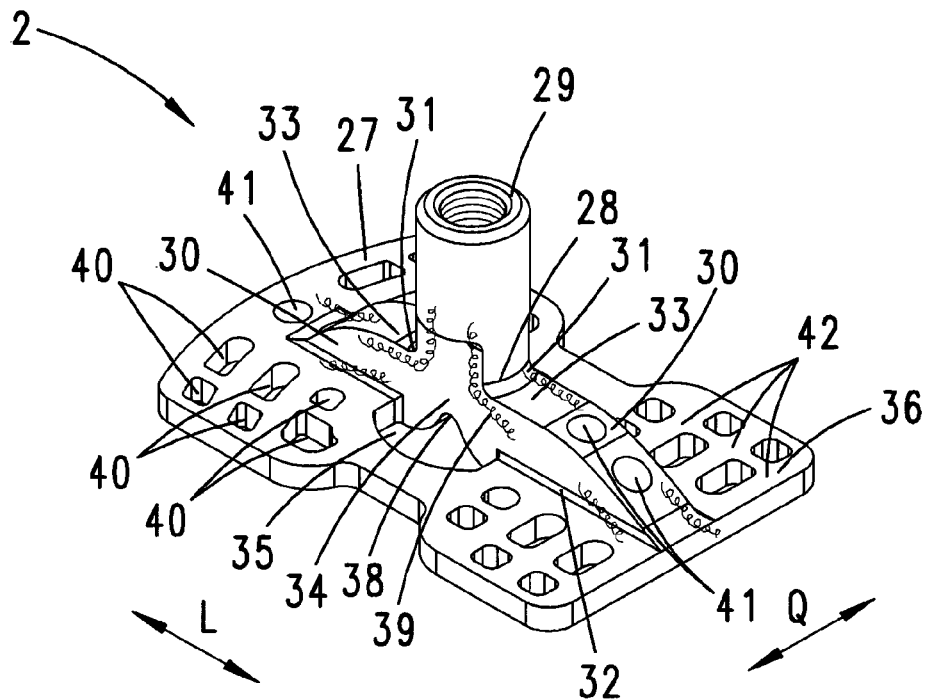
FIG. 10 shows in perspective a foot part according to a preferred embodiment.

FIG. 1 shows in perspective the implant 1 according to the invention as provided by a first preferred embodiment. This is a jaw implant with a basal, plate-like foot part 2, which in the example is circular, and a cylindrical shaft 3, which is formed in one part with the foot part or is connected to it and, from the center of the foot part, extends in its longitudinal direction perpendicularly to the plane of the foot part. The foot part 2 can be laterally inserted into a cavity milled in the jaw, where it serves for basal anchorage of the jaw implant. During the fitting of the one-piece implant that is shown here by way of example, the shaft 3 is likewise pushed laterally into a prepared jaw cavity, so that for example an artificial tooth or a prosthetic dental construction can be secured on the threaded zonal portion 4 that is provided at the upper end. The implant 1 is produced substantially from a structural material which predominantly contains polyetherether ketone or a mixture of polyetherether ketones differing for example in chain length or structure and to which, optionally, certain additives are added to influence the material properties, the aforementioned composition of the base material being selected here to be the same throughout for the foot part 2 and the shaft 3. In the exemplary embodiment shown in FIG. 1, the foot part 2 forms by way of example, for the purposes of the invention, a first structural region 5 and the shaft 3 forms a second structural region 6, in each case for implantation in the jaw bone. In order that the different structural regions 5 and 6 differ in their material properties, helically coiled fiber-like filaments 7 are added to the structural material in the region of the foot part 2, i.e. the first structural region 5, the form, size, amount and distribution within the foot part 2 of which filaments is merely schematically indicated in FIG. 1 (and in the following figures). The filaments 7 may be disposed such that they are either evenly or unevenly distributed within the foot part 2, although this and the proportion in terms of the amount are not qualitatively illustrated in the representation but instead variations are possible according to requirements. The helically coiled filaments 7 provided as inclusions in the foot part 2 in FIG. 1, which in the example are carbon fibers, have the effect of forming a composite material which has different material properties than the base material without the filaments 7. Specifically, the resistance to torsion is improved by the helically coiled filaments 7, which may be advantageous in particular for fitting of the jaw implant in the lower jaw posterior region.

FIG. 2 shows in perspective a second preferred embodiment of the implant 1 according to the invention, the same reference numerals being used here (and hereafter) for features that are comparable to one another to provide a better overview. One difference with respect to FIG. 1 is that the implant 1 shown in FIG. 2 it is a multi-part implant. For this purpose, the shaft 3 has in addition to the threaded zonal portion 4 located at the upper end (for example for an artificial tooth), a threaded zonal portion 4 located in the middle region and a threaded zonal portion 4 located at the lower end. The threaded zonal portions 4 are spaced apart from one another by two smooth annular zones 8, the diameter of which is somewhat smaller than the root of the thread. For securing to the plate-like foot part 2, the shaft 3 is screwed by the lower threaded zonal portion 4 into a matching internally threaded zonal portion 9 (cf. also FIG. 3) in the foot part 2. An intermediate part 10, which is likewise like a plate and projects less far toward the peripheral edges in comparison with the foot part 2, is screwed onto the middle threaded zonal portion 4 by means of a likewise matching internally threaded zonal portion 11. For this purpose, the intermediate part 10 may, for example, first be screwed over the upper threaded zonal portion 4 of the shaft 3, then displaced over the upper smooth annular zone 8 and subsequently screwed onto the middle threaded zonal portion 4, thereby producing to this extent a variable, i.e. adjustable, spacing with respect to the foot part 2. In the case of the second exemplary embodiment, shown in FIGS. 2 and 3, the foot part 2 (or else for example part of the same) may, for the purposes of the invention, be regarded as the first structural region 5, the shaft 3 (or else for example part of the same) may be regarded as the second structural region 6 and the intermediate part 10 (or else for example part of the same) may be regarded as a third structural region 12, a structural material based on polyetherether ketones once again being used throughout. In order to give the different structural regions different material properties, they are provided with different additives. As schematically indicated, the structural material in the foot part 2 contains plain, i.e. substantially straight, filaments 13, by which the stability of the base plate is increased and by which in particular adaptation of the modulus of elasticity to the surrounding jaw bone can be achieved. In the second structural region 6 (in the shaft 3), helically coiled filaments 7 are added to the structural material, in order to improve the possibility of deflections of the thread carrier of, for example, up to 150 μm during the act of chewing and springing back into the starting position and to achieve the necessary resistance to rupture. To this extent, the elastic behavior can be improved and the elasticity can be matched to the surrounding body tissue. Taking the loads occurring into consideration, the implant 1 described with reference to FIGS. 2 and 3 offers advantages on account of the features and properties described, in particular when it is fitted in the upper jaw, especially in the upper jaw posterior region. Depending on requirements, it may also be possible in this case to dispense with the intermediate part 10 or optionally to fit a further intermediate part. On account of the cross-hatching, the plain filaments 13 are not included in the illustration in FIG. 3, but the schematic representation selected in FIG. 2 shows that they are present throughout, not only at the surface but also in the interior of the foot part 2.

FIG. 4 shows the implant 1 according to the invention as provided by a further preferred, once again one-piece, embodiment. The production as one part creates the possibility of helically coiled filaments 7 extending from the foot part 2 into the shaft 3 continuously (likewise in one piece) within the surrounding structural material. At the transition from the foot part 2 to the shaft 3, which is relatively fragile even in the case of the one-part configuration on account of the strong cross-sectional transition, these filaments form as it were an elastic reinforcement, and thereby reduce the risk of rupture. The coiled filaments 7 in the said transitional region have the effect of helping the shaft 3 to deflect during the act of chewing and subsequently spring back into the starting position, i.e. they have the effect of improving the elastic behavior. The radially inner foot part region adjoining the lower end of the shaft 3 and enclosed by the circular reference line 14, in which region the coiled filaments 7 are anchored, has different material properties in comparison with the foot part region adjoining the line 14 radially outwardly. To this extent, in the case of the exemplary embodiment of FIG. 4, the foot part regions on the one hand inside the circular reference line 14 and on the other hand outside the circular reference line 14 may be regarded for the purposes of the invention, as different structural regions 5, 15, with different material properties from one another. This means that on the foot part 2 there are different structural regions with different material properties from one another. The implants described with reference to FIGS. 1 to 4 are not restricted to the geometric forms respectively represented but may, in the same way as the shaft, also be of different shapes and/or sizes. In particular, the foot and/or intermediate parts may also have contours that differ in virtually any desired way and, for example, also cutouts on the inside and/or at the periphery.

FIG. 5 shows in perspective a further preferred embodiment of a multi-part implant 1 according to the invention. With regard to the multi-part form and the screw connections selected for the connection of the components, the configuration can be compared with the variant shown in FIG. 2. However, differences in the configuration of foot part 2 and intermediate part 10 are evident. Even in the case of the modification selected in FIG. 5, each substantially comprises a flat plate-like body. In both cases, this has a peripheral region 16 which runs around somewhat in the form of a horseshoe and is closed by an outer web 17. The opposing longitudinal sides 18 of the foot part 2 are connected by a bridge-like inner web 19 and the opposing longitudinal sides 20 of the intermediate part 10 are connected by a bridge-like inner web 21, in each case integrally in the manner of pairs. In the center of the inner web 19 there is the blind hole that can be seen in section in FIG. 6, with an internally threaded zone 9 for the screw connection to the shaft 3, while a through-hole (cf. FIG. 6) with an internally threaded zone 11 is provided in the center of the inner web 21. On both sides of the inner web 19 or 21, the foot part 2 or intermediate part 10 has through-openings that are enclosed by the edge running around the periphery. The perpendicular thread carrier 3, which is connected at the lower threaded zonal portion 4 to the base plate 2, has helically coiled filaments 7 interspersed within it over its entire length and, as a result, can be provided with elastic properties that are sensitive to the lateral deflectability of the periodontal apparatus. With regard to its multi-part form, the implant 1 represented in FIGS. 5 and 6 may also be referred to as a so-called modular implant, the possibility also existing if need be for one or more components to be exchanged for others. Alternatively, however, the implants shown in FIGS. 5 and 6 could also be produced in one piece.

In FIG. 7, the foot part 2 already shown in FIGS. 5 and 6 is represented in plan view. To give the foot part 2 different material properties in different regions, plain filaments 13 have been respectively added to the polyetherether ketone serving as the base material in the periphery 16 that extends in the shape of a horseshoe and in the outer web 17 closing the latter. It is schematically indicated by the representation that a lower concentration of straight filament inclusions 13 has been selected in the peripheral region that includes the outer web 17 and the part of the horseshoe-like periphery 16 extending from there to the geometrical reference line 22 than in the peripheral region running from the line 22 to the vertex 23 of the rounded portion, the reference line 22 approximately bisecting the cutout in the foot part 2 remote from the vertex. The comparatively greater addition of plain inclusions 13 allows the part of the basal plate that is rounded off toward the vertex 23 through to the reference line 22 to be made less elastic than the frame lying on the other side of the reference line 22 and to be made similar in its elastic behavior in particular to the cortical bone on the lingual side of the jaw. To this extent, the frame part lying on the left side of line 22 in the viewing direction of FIG. 7 can be regarded for the purposes of the invention as a structural region 24 with associated material behavior and the outer frame lying to the right of the line 22 in the viewing direction can be regarded as a further structural region 25 with different material properties than the structural region 24. The side of the foot part that is adapted by the rounded portion to the lingual side of the jaw can consequently be stiffer than the opposite side of the foot part in the region of the outer web 17 that is adapted to the buccal side of the jaw bone. It was stated with reference to FIG. 5 that the shaft 3, as the perpendicular thread carrier, may have lower brittleness and higher elasticity in comparison with the foot part 2, as the basal plate, by means of the coiled inclusions 7 incorporated in it. FIG. 7 reveals that helically coiled filaments 7 are also incorporated in the surrounding plastics on the foot part 2 in the region of the bridge-like inner web 19, which forms a cross-piece carrying the thread carrier 3, in order to make the cross-piece 19 comparatively more elastic. These regions can to this extent be regarded for the purposes of the invention as structural regions 26 with material properties different from other structural regions within the same component.

FIGS. 8 and 9 show preferred modifications of the foot part 2 shown in FIG. 7. In FIG. 8, the inner web 19 has been offset in comparison with FIG. 7 by about one third of the overall length from the rounded longitudinal end in the direction of the substantially linearly-bounded longitudinal end, so that the distance now from the latter is about one third of the overall length.

FIG. 9 relates to a configuration in which both of the inner webs 19 shown in FIGS. 7 and 8 are present.

Figure 11:
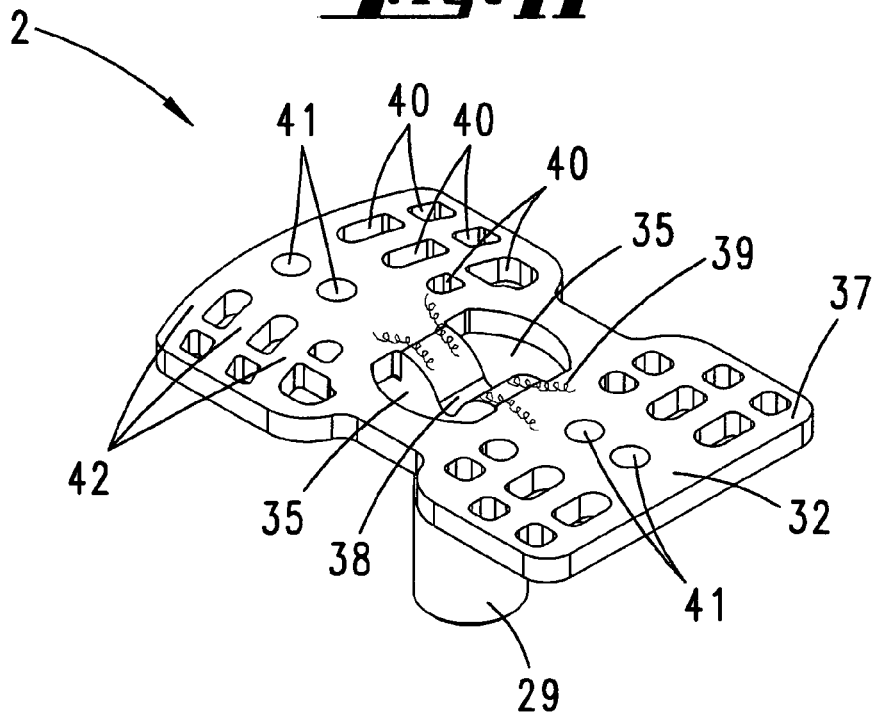
FIG. 11 shows the foot part shown in FIG. 10 in an inverted position.

FIGS. 10 and 11 show in perspective a foot part 2 according to a further preferred embodiment. This is configured in one piece and has a plate-like base part 27 and a connecting part 28, specifically a threaded connecting part 29 for connection of a shaft that is not represented (cf. however FIG. 14 for example), of an abutment, or the like. Furthermore, there are two reinforcing webs 30 rising up above the plate-like base part, which webs respectively merge at their longitudinal end 31 facing the center of the foot part into the connecting piece 28 and extend in the direction of a middle region 32 that is oriented in a longitudinal direction L of the base part 27. As from a certain distance from the connecting piece 28, the upper edge 33 of the reinforcing webs 30 descends in a rounded manner as it extends further away from the said connecting piece, down to the upper surface 36 of the base part as seen in the viewing direction of FIG. 10. The reinforcing webs 30 are of different lengths, the reinforcing web that is facing a convexly rounded transverse edge at the front in the direction of insertion of the implant being shorter and leaving a web-free periphery of the base part 27. The reinforcing webs 30 merge into one another in a central connecting region 34. On both sides thereof, the base part 27 has approximately semicircularly contoured central through-openings 35. The surface 37 of the base part that is lying on the side of the foot part opposite from the reinforcing webs 30 has in the connecting region 34 a depression 38, which is rounded symmetrically in the longitudinal direction L up to a shallow vertex and extends beyond the plate surface 36 facing the reinforcing ribs into the connecting region 34. As a result, the reinforcing webs 30 have as it were the form of legs, which serve for the uniform load transfer from a connected shaft or the like to the base part and which can thereby also assume the function in particular of resilient carriers. In the exemplary embodiment selected, inclusions comprising helically coiled fiber material 39 are embedded in the surrounding material, which is polyetherether ketone (PEEK), in the region of the reinforcing webs to help provide this property. As can be seen, the reinforcing webs have a rectangular cross-section. It is schematically indicated that the fiber material 39 extends in its longitudinal extent predominantly in the longitudinal direction L of the reinforcing webs and, at the peripheral edges with respect to the base part 27, reaches into the threaded connecting piece 29. The plate-like base part 2 has through-openings 40. Formed in each of the four corner regions is a group of six openings 40, which are respectively spaced apart from one another in pairs in the longitudinal direction L and within pairs in the transverse direction Q. Bounded by the through-openings are ribs 42, which run substantially in the longitudinal direction L and facilitate the detachment of regions of the base part (symmetrically or unsymmetrically) for adaptation to anatomical conditions. This applies correspondingly to the further ribs, then running transversely, i.e. in the longitudinal direction L. Spaced apart along the middle region 32 in the base part 27 are four cylindrical through-holes 41, which, depending on their position, also extend through the reinforcing webs 30. As still to be explained below, the through-holes 41 may, if need be, be used together with the threaded connecting piece 29 for the connection of preferably pin-like connecting elements, so that a number of foot parts 2 can be connected to one another in a variety of different ways.

Figure 12:
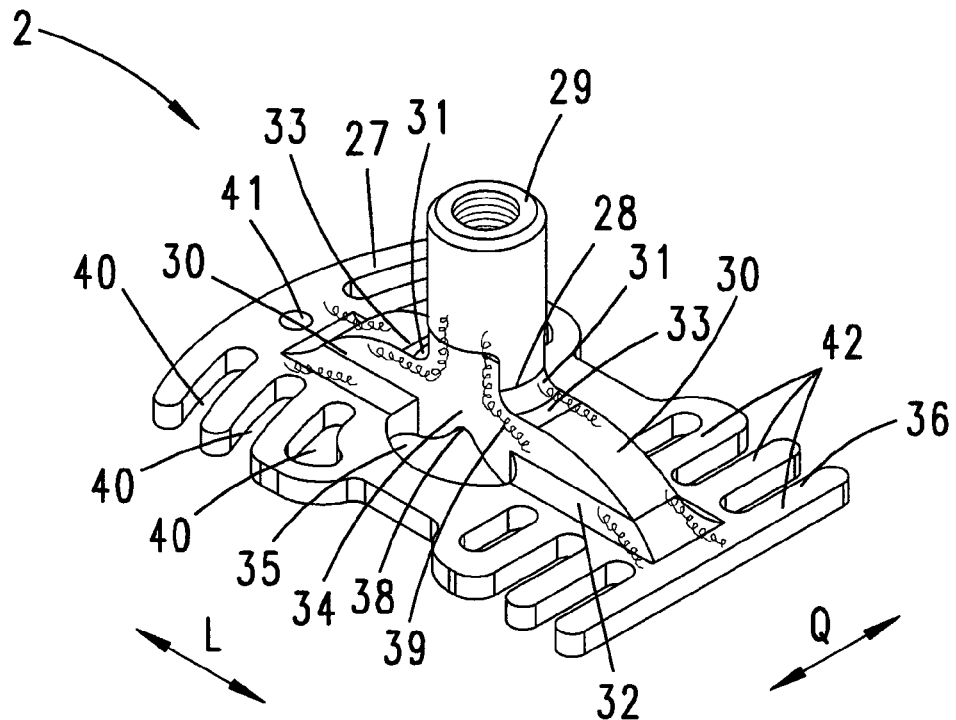
FIG. 12 shows in perspective a foot part according to a further preferred embodiment.
Figure 13:
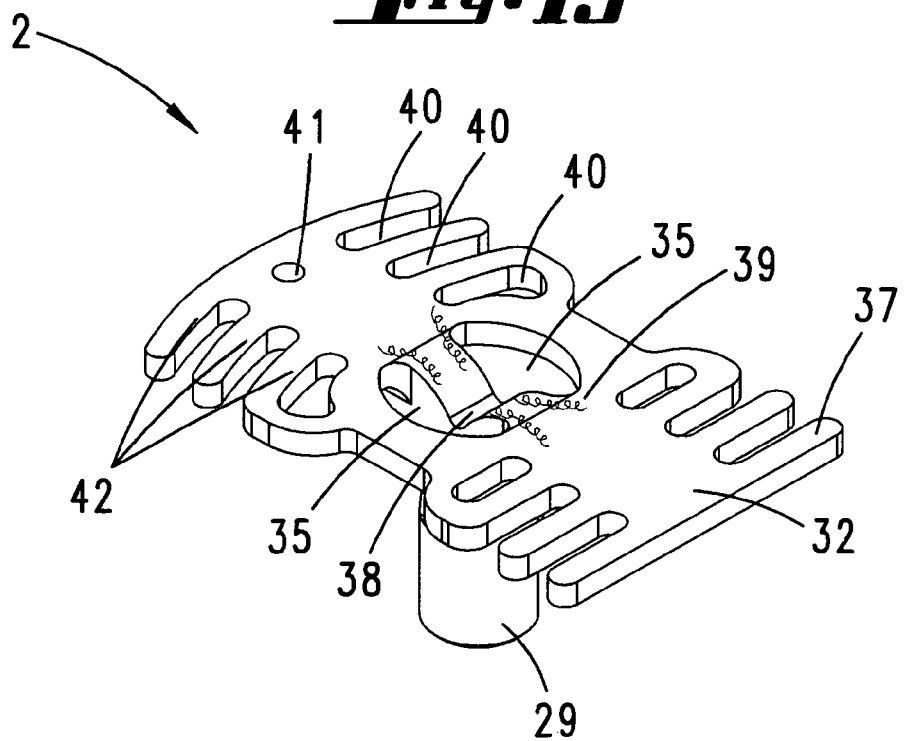
FIG. 13 shows the foot part shown in FIG. 12 in an inverted position.

FIGS. 12 and 13 show a further preferred embodiment of the foot part 2 within the scope of the invention, the same reference numerals being retained here, as before, for corresponding or comparable details in order to maintain an overview. The difference from the previous embodiment is that the outer ribs 42 in the longitudinal direction L have free ends.

Figure 14:
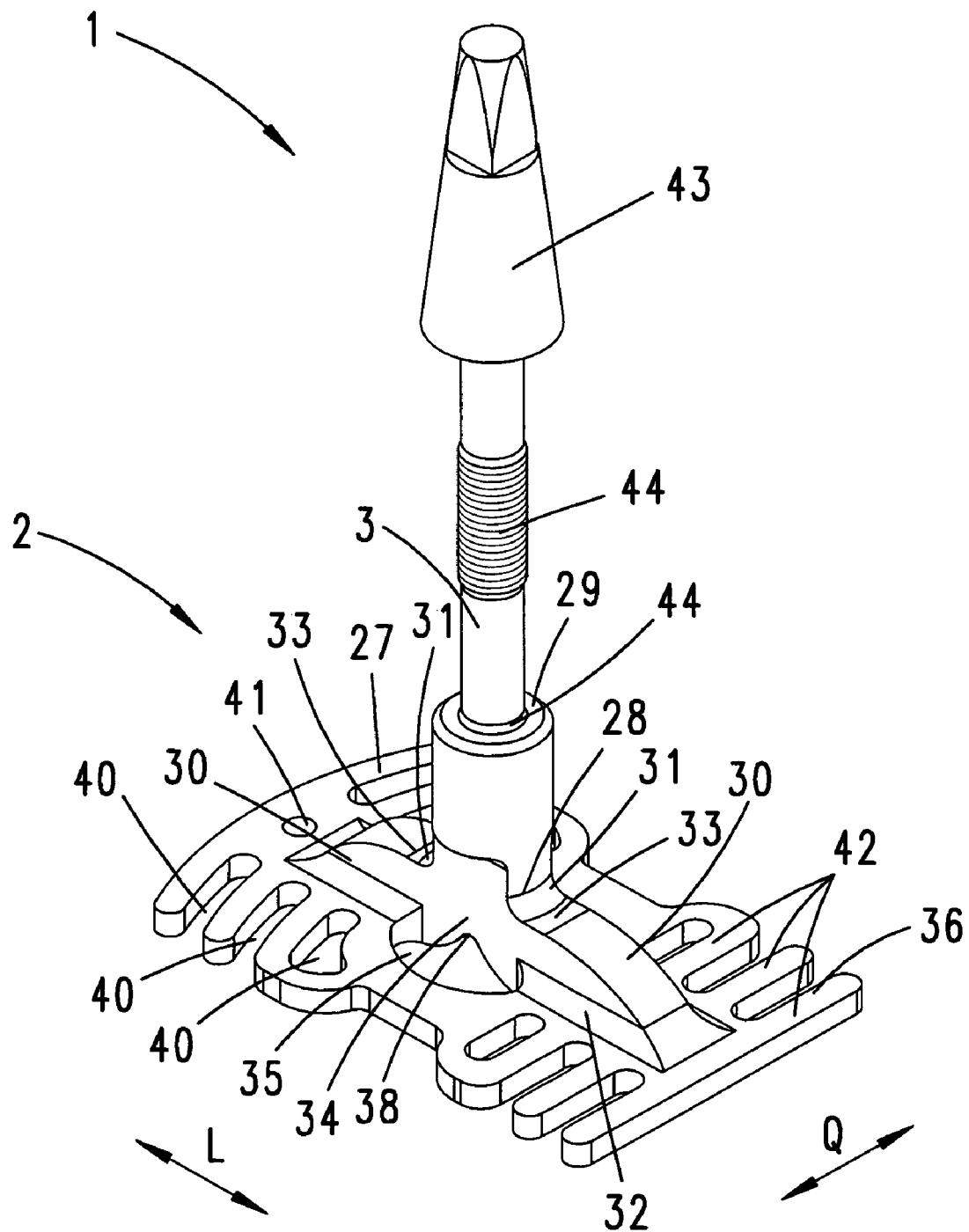
FIG. 14 shows in perspective an implant according to the invention as provided by a further preferred embodiment.

FIG. 14 shows an implant 1 according to the invention as provided by a further preferred embodiment. In this case, a shaft 3 has been screwed into the foot part 2, shown in FIGS. 12, 13, by means of a threaded portion 44 on the end of the said shaft. At the opposite longitudinal end there is a conical so-called abutment 43, which is suitable for receiving or providing a base for a crown, a prosthetic part or the like. The shaft 3 also has about halfway along it a second threaded zonal portion 44, on which a further plate part (intermediate part), provided with a continuous thread, may be held in a height-adjustable manner if need be. In the example selected, the foot part 2 and the shaft 3 are produced from a material based on polyetherether ketone (PEEK). The material used for the shaft 3 has a modulus of elasticity of about 4 GPa. By contrast, the foot part 2 is produced as a whole from polyetherether ketone reinforced by means of carbon fibers (not pictorially represented), in particular by means of plain or non-coiled fibers, and has a modulus of elasticity of about 11 GPa.

Figure 15:
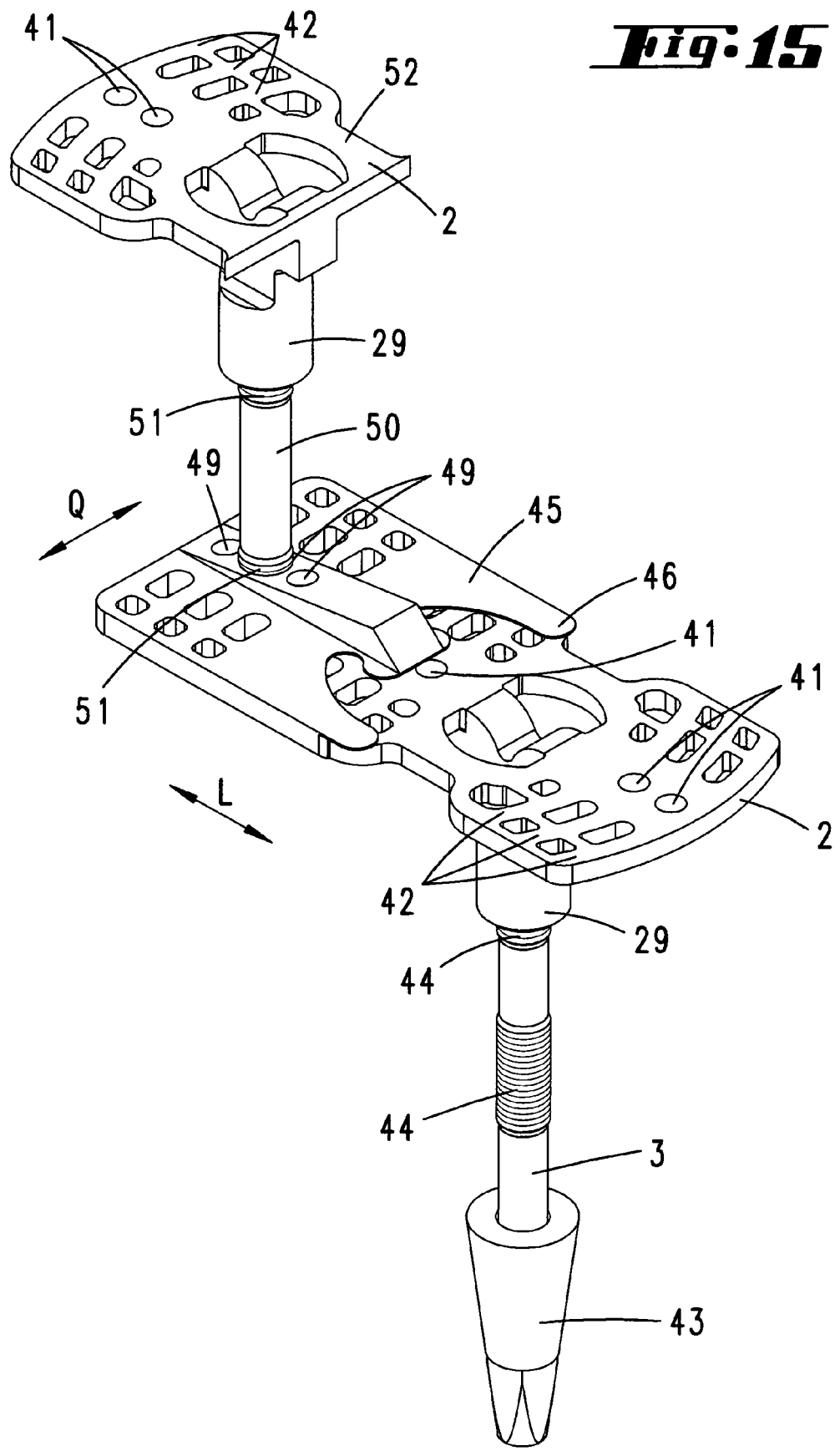
FIG. 15 shows in perspective an implant according to the invention as provided by a further preferred embodiment and FIG. 16 shows the sleeve part according to FIG. 15.

FIG. 15 shows in perspective the implant 1 according to the invention as provided by a further preferred embodiment. This also has the shaft 3 described with reference to FIG. 14, which has been screwed into the foot part 2 described in relation to FIGS. 10, 11, specifically in the threaded connecting piece 29 of the latter. This foot part 2 forms together with the sleeve part 45, also shown in FIG. 16, a first mount 46, which is also plate-like as a whole. The sleeve part 45 is positively held on the foot part 2, in that a boss 48 that rises up from a resilient tongue 47 and is similar to a segment of a sphere first gives way in a compliant manner when the foot part is inserted and then, as it is covered over, is pressed by the resilient tongue into a through-hole 41. In addition, the sleeve part 45 is adhesively cemented to the foot part 2. The sleeve part 45 has in its middle region a row of three spaced-apart through-holes 49, which are oriented in the longitudinal direction L. In the example selected, a cylindrical connecting element 50 has been screwed into the middle one of the three holes 49, for the adaptation to anatomical conditions, an internal thread, that is not represented, having been cut into the hole 49 by the threaded zonal portion 51 of the said element in a self-tapping manner. At the other longitudinal end, the connecting element 50 has been screwed into the threaded connecting piece 29 of a further foot part 2, which forms a second plate-like mount 52. The foot part 2 thereof differs from the foot part 2 of the first mount 46 in that it has been shortened in the longitudinal direction for the adaptation to anatomical conditions. The first mount 46 can preferably be laterally inserted, at least with a portion of the plate, into a groove milled in the jaw bone region. To provide additional retention, the second mount 52 can be inserted into a further milled groove, for example in the region of the yoke piece. The sleeve part 45 serves for lengthening the connecting plane of the first mount 46, i.e. makes it possible to have a greater lateral distance between the longitudinal directions of the shaft 3 and of the connecting element 50 that are oriented parallel to one another in the example. It goes without saying that, depending on requirements, if only a relatively small lateral distance is required, it would be possible to dispense with the sleeve part 45 and instead, for example, screw the connecting element 50 into a through-hole 41 of the foot part 2 of the first mount. The threaded connecting piece 29 and the through-holes 41 and 49 are connections which, overall, are distributed respectively on the mounts 46, 52 and are suitable for connecting the shaft 3 and the connecting element 50 according to choice. In the example selected, the shaft 3 and the connecting element 50 respectively extend perpendicularly to the planes of principal extent of the first and second mounts 46, 52 and on geometrical spatial lines that are spaced apart parallel to one another.

Figure 16:
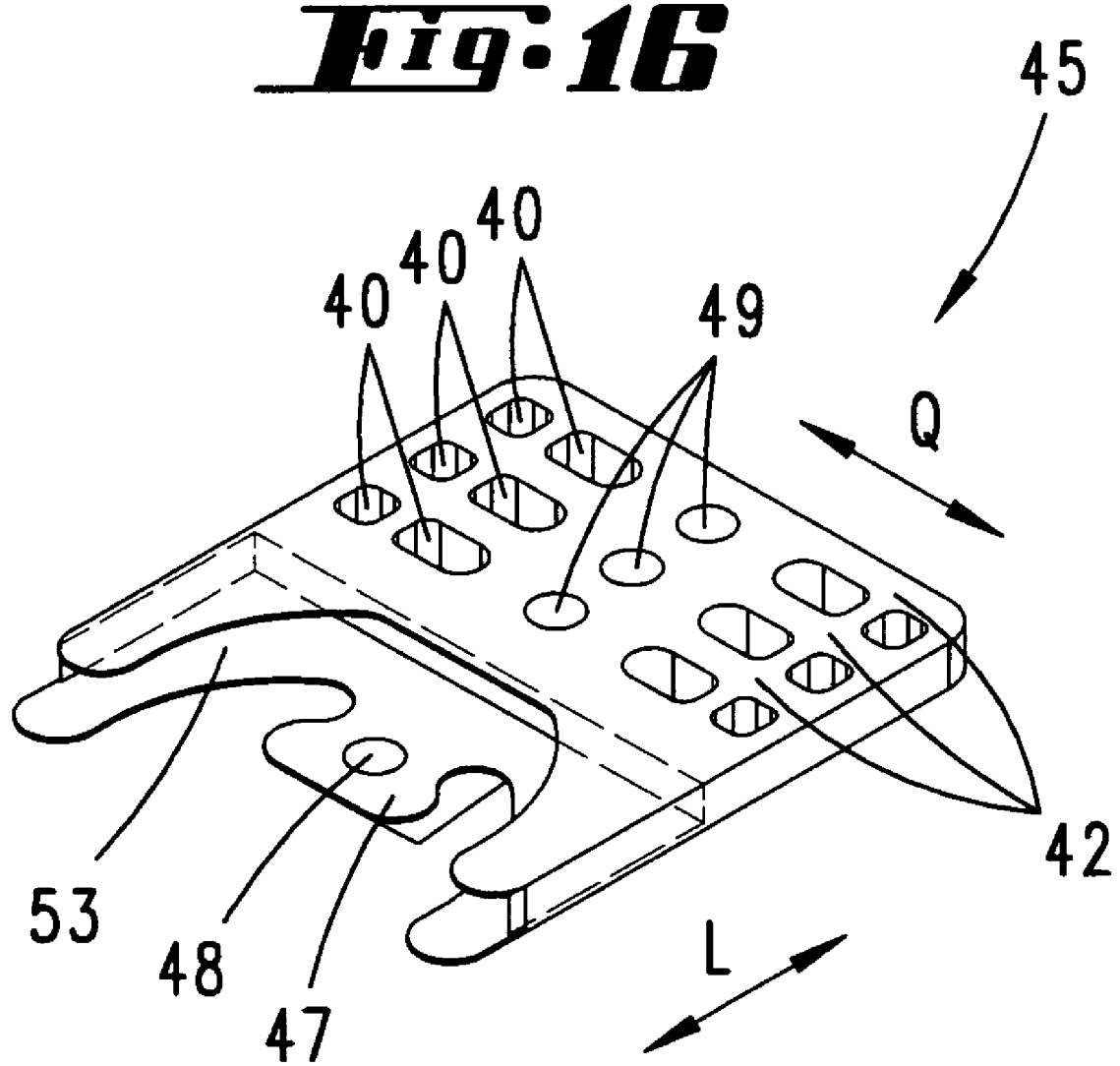

FIG. 16 illustrates the pocket-like recess 53 which is formed on the sleeve part 45 and a hollow pocket cross-section of which is adapted to the cross-section of the foot part 2 transversely to the longitudinal direction L, i.e. has the same width and height as the said foot part, to achieve a positive plug-in mounting. In the case of the implant shown in FIG. 15, the shaft 3, the connecting part 50, the two foot parts 2 and the sleeve part 45 are produced from a plastics which contains polyetherether ketone. The shaft 3 and the connecting part 50 in this case consist of homogeneous plastics and have in the example selected a modulus of elasticity of about 4 GPa. In the case of the sleeve part 45 and the foot part 2 of the first mount 46, the polyetherether ketone as a whole is glass fiber reinforced, in particular by using plain or non-coiled fibers (not pictorially represented), and has a modulus of elasticity of about 11 GPa. Merely by way of example, the foot part 2 of the second mount 52 is carbon reinforced (fibers not pictorially represented) and likewise has a modulus of elasticity of about 11 GPa. Alternatively, for example, the first mount 46 could also consist of carbon reinforced polyetherether ketone, and it goes without saying that numerous further modifications beyond this would also be possible. In particular, in the case of the exemplary embodiments of FIGS. 14, 15, the foot parts 2 may additionally have the coiled fibers 39 shown in FIGS. 10-14, or it is possible to dispense with them.

All features disclosed are (in themselves) pertinent to the invention. The disclosure content of the associated/accompanying priority documents (copy of the prior patent application) is also hereby incorporated in full in the disclosure of the application, including for the purpose of incorporating features of these documents in claims of the present application.

The invention claimed is:

1. A jaw implant having a number of structural regions which are made of a material that cannot be resorbed by bones, or not to any substantial extent, and are suitable for implantation in or at least alongside bones, two or more of these structural regions having physical material properties that are different from one another, wherein the jaw implant is produced from stiffer material on one side than on an opposite side, which one side is geometrically adapted for implantation on a lingual side of the jaw, and which opposite side is geometrically adapted by comparison for implantation on a buccal side of the jaw; and wherein the jaw implant has as component parts at least one basal foot part and a shaft extending from the at least one basal foot part, wherein the shaft has lower brittleness and/or higher or more pronounced elasticity in comparison with the at least one basal foot part as a result of spiral and/or helically coiled fibrous filaments contained therein or as a result of a higher amount of such fibrous filaments in comparison with the at least one basal foot part.

2. The jaw implant according to claim 1, wherein the jaw implant has in the two or more different structural regions a different level of modulus of elasticity, and/or different viscoelastic behavior and/or different toughness and/or different stiffness and/or different flexural strength and/or different torsional strength, and/or different hardness and/or different brittleness from one another.

3. The jaw implant according to claim 1, wherein the jaw implant is produced at least partially from a polyetherether ketone, mixtures of different polyetherether ketones, or a plastics material.

4. The jaw implant according to claim 3, wherein in one or more structural regions there is added to the plastics material, the polyetherether ketones or the mixture of polyetherether ketones, at least one additive, the at least one additive being fibrous filaments in the form of carbon fibers and/or glass fibers and/or titanium fibers, and/or one or more non-fibrous additives.

5. The jaw implant according to claim 1, wherein plain and/or spirally and/or helically coiled fibrous filaments are contained in one or more structural regions.

6. The jaw implant according to claim 1, wherein to achieve different material properties in different structural regions of the jaw implant, different polyetherether ketones or different mixtures of polyetherether ketones, are provided and/or the type and/or amount of additives is differently selected.

7. The jaw implant according to claim 1, wherein the jaw implant is a one-part or multi-part jaw implant that can be basally anchored.

8. The jaw implant according to claim 1, wherein plain and/or spiral and/or helically coiled filaments are contained in at least one basal foot part.

9. The jaw implant according to claim 1, wherein the at least one basal foot part is plate-like.

10. The jaw implant according to claim 8, wherein the at least one basal foot part is plate-like.

* * * * *